(12) United States Patent
Smith et al.

(10) Patent No.: US 10,086,065 B2
(45) Date of Patent: *Oct. 2, 2018

(54) RABIES GLYCOPROTEIN VIRUS-LIKE PARTICLES (VLPS)

(71) Applicant: NOVAVAX, INC., Gaithersburg, MD (US)

(72) Inventors: Gale Smith, Germantown, MD (US); Ye Liu, Clarksville, MD (US)

(73) Assignee: Novavax, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,955

(22) Filed: Jun. 30, 2017

(65) Prior Publication Data

US 2018/0021428 A1    Jan. 25, 2018

Related U.S. Application Data

(63) Continuation of application No. 13/883,745, filed as application No. PCT/US2011/059602 on Nov. 7, 2011, now Pat. No. 9,724,405.

(60) Provisional application No. 61/410,767, filed on Nov. 5, 2010.

(51) Int. Cl.
| | | |
|---|---|---|
| *C07K 14/005* | (2006.01) | |
| *A61K 39/205* | (2006.01) | |
| *A61K 39/12* | (2006.01) | |
| *A61K 39/00* | (2006.01) | |

(52) U.S. Cl.
CPC ............ *A61K 39/205* (2013.01); *A61K 39/12* (2013.01); *C07K 14/005* (2013.01); *A61K 2039/5258* (2013.01); *A61K 2039/55505* (2013.01); *C12N 2760/20134* (2013.01); *C12N 2799/026* (2013.01)

(58) Field of Classification Search
None
See application file for complete search history.

(56) References Cited

U.S. PATENT DOCUMENTS

| | | |
|---|---|---|
| 5,667,782 A | 9/1997 | Roy |
| 6,673,601 B1 | 1/2004 | Jacob et al. |
| 7,235,245 B2 | 6/2007 | Jacob et al. |
| 8,535,650 B2 | 9/2013 | Constantinides et al. |
| 8,715,738 B2 | 5/2014 | Chung et al. |
| 9,724,405 B2 * | 8/2017 | Smith ............... A61K 39/12 |
| 2004/0014708 A1 | 1/2004 | Piebanski |

(Continued)

FOREIGN PATENT DOCUMENTS

| | | |
|---|---|---|
| EP | 0237686 A1 | 9/1987 |
| WO | WO 2009/153801 A1 | 12/2009 |

(Continued)

OTHER PUBLICATIONS

Benmansour et al., "Antigenicity of rabies virus glyprotein", J. Virol., 1991, 65(8):4198-4203.

(Continued)

*Primary Examiner* — Michelle S Horning
(74) *Attorney, Agent, or Firm* — Cooley LLP

(57) ABSTRACT

The present invention is generally related to virus-like particles (VLPs) comprising rabies virus (RV) glycoproteins (G proteins) and methods for making and using them, including immunogenic compositions such as vaccines for the treatment and/or prevention of rabies virus infection.

14 Claims, 6 Drawing Sheets

Specification includes a Sequence Listing.

(56) References Cited

U.S. PATENT DOCUMENTS

| | | | |
|---|---|---|---|
| 2005/0064389 | A1 | 3/2005 | Jacob et al. |
| 2005/0079145 | A1 | 4/2005 | Constantinides et al. |
| 2009/0010963 | A1 | 1/2009 | Wu et al. |
| 2009/0263420 | A1 | 10/2009 | Morrison et al. |
| 2010/0166769 | A1 | 7/2010 | Hsiao et al. |
| 2010/0143406 | A1 | 10/2010 | Smith et al. |
| 2010/0167341 | A1 | 10/2010 | You et al. |
| 2010/0267116 | A1 | 10/2010 | Kawaoka et al. |
| 2010/0291040 | A1 | 11/2010 | Lobel et al. |
| 2014/0178419 | A1 | 6/2014 | Smith et al. |

FOREIGN PATENT DOCUMENTS

| | | |
|---|---|---|
| WO | WO 2010/040023 A2 | 4/2010 |
| WO | WO 2010/077717 A1 | 7/2010 |

OTHER PUBLICATIONS

Berezin et al., "Controlled organization of multimolecular complexes of enveloped virus glycoproteins: study of immunogenicity," Vaccine 6:450-456 (1988).

International Search Report dated Oct. 24, 2012 in PCT appl. No. PCT/US11/059602, 5 pages.

Fekadu et al., "An immune stimulating complex (ISCOM) subunit rabies vaccine protects dogs and mice against street rabies challenge," Vaccine 10:192-197 (1992).

Fu et al., "Oral vaccination of racoons (Procyon lotor) with baculovirus-expressed rabies virus glycoprotein)," Vaccine 11(9):925-928 (1993).

Genbank Direct Submission ACR39382.1, Glycoprotein [Rabies virus], May 31, 2009, [Retrieved from the internet May 7, 2012; <http://www.ncbi.nim.nih.gov/protein/ACR39382.1>.

Kang et al., "Influenza Virus-Like Particles as Pandemic Vaccines. Current Topics in Microbiology and Immunology", Vaccines for Pandemic Influenza, 2009, 333(3):269-289.

Marissen et al., "Novel rabies virus-neutralizing epitope recognized by human monoclonal antibody: fine mapping and escape mutant analysis", J. Virol., 2005, 79(8):4672-8.

Morein et al., "Subunit vaccines against enveloped viruses: virosomes, micelles and other prtoein complexes," Vaccine 3:83-93 (1985).

Perrin et al., "Rabies immunosome (subunit vaccine) structure and immunogenicity. Pre- and post-exposure protection studies" Vaccine, 1985, 3(3):325-332.

Prehaud et al., "Immunogenic and Protective Properties of Rabies Virus Glycoprotein Expressed by Baculovirus Vectors," Virology 173:390-399 (1989).

Ramya et al., "Expression and Solubilization of Insect Cell-Based Rabies Virus Glycoprotein and Assessment of Its Immunogenicity and Protective Efficacy in Mice," Clin. Vaccine Immunol.18(10):1673-1679 (2011).

Roy et al., "Virus-like particles as a vaccine delivery system: myths and facts", Hum. Vaccin., 2008, 4(1):5-12.

Scheerlinck et al., "Virus-sized vaccine deliver systems," Drug Discov. Today, 2008 13(19-20):882-887.

Simons et al., "Formation of protein micelles from amphiphilic membrane proteins," Proc. Natl. Acad. Sci. USA75(11):5306-5310 (1978).

Supplementary European Search Report, EP appl. No. 11838942.8, 11 pages (dated Mar. 3, 2014).

Sureau et al., "The use of immunosome technology for vaccines against rabies and other viral diseases", Eur J. Epidemiol., 1989, 5(3):275-278.

Swenson et al., "Generation of Marburg virus-like particles by co-expression of glycoprotein and matrix protein", FEMS Immunol. Med. Microbiol. 2004, 40(1):27-31.

Tuchiya et al., "Characterization of rabies virus glycoprotein expressed by recombinant baculovirus," Virus Res. 25:1-13 (1992).

UniProtKB—P08867 (GLYCO_RABVP), Last modified: Jan. 1, 1988, Accession No. P08667 (Date of search: Oct. 22, 2015), http://www.uniprot.org/uniprot/P08667, 5 pages.

Dow Chemical, "TERGITOL™ NP-9 Surfactant. Product Information," 2 pages (Nov. 2009).

Durrer et al., "Photolabeling Identifies a Putative Fusion Domain in the Envelope Glycoprotein of Rabies and Vesicular Stomatitis Viruses," J. Biol. Chem. 270(29):17575-17581 (1995).

European Search Report, EP appl. No. 17179212.0, 10 pages (dated Oct. 9, 2017).

Ramya et al., "Expression and Solubilization of Insect Cell-Based Rabies Virus Glycoprotein and Assessment of Its Immunogenicity and Protective Efficacy in Mice," Clin. Vaccine Immunol. 18(10):1673-1679 (2011).

\* cited by examiner

FIGURE 2

| Sample | Lot | Sample ID | BCA-mg/ml | DNA-µg/ml | BV ELISA-µg/ml |
|---|---|---|---|---|---|
| 2 | 031810 | Rabies G839 | 0.39 | 0.34 | 5.5 |

| Sample | Lot | Sample ID | Sterility | LAL EU/ml | Plaque pfu/ml |
|---|---|---|---|---|---|
| 2 | 031810 | Rabies G839 (2L) | negative | 0.41 | ND @10⁻¹ and 10⁻² |

| Sample ID Lot# | Description | Lane | Band | MW | % Band Purity |
|---|---|---|---|---|---|
| 031810 | Rabies G839 | 4 | Rabies | 54.0 | 85.2 |
| 031810 | Rabies G839 | 5 | Rabies | 54.6 | 66.1 |

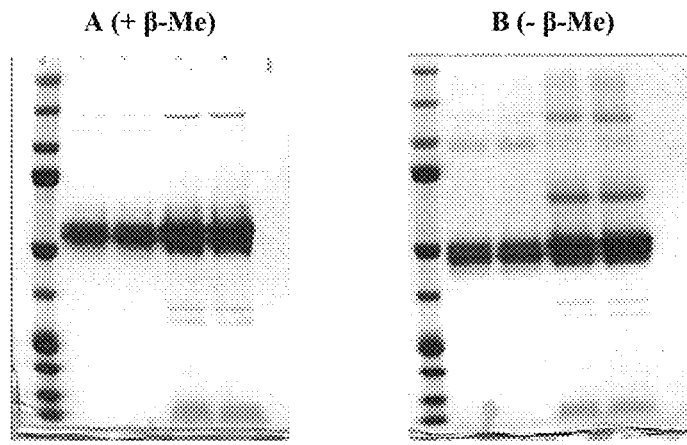

A (+ β-Me)    B (- β-Me)

Lane 1: Precision Plus Protein Standard
Lane 2: RV G Protein (Lot 021610)
Lane 3: RV G Protein (Lot 021610)
Lane 4: RV G Protein (Lot 031810)
Lane 5: RV G Protein (Lot 031810)

FIGURE 4
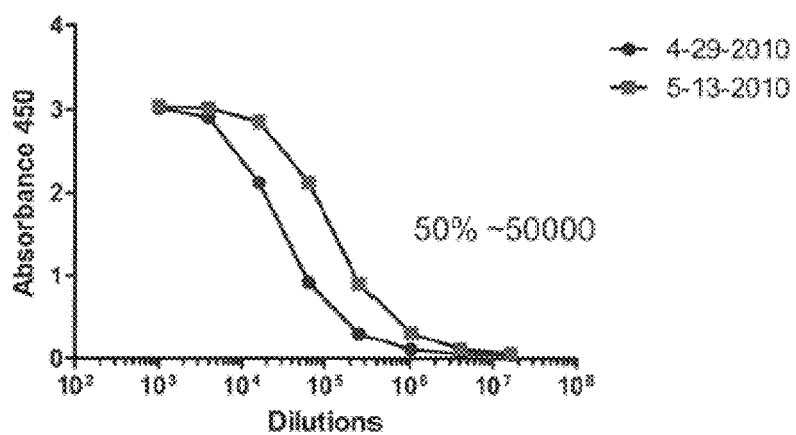
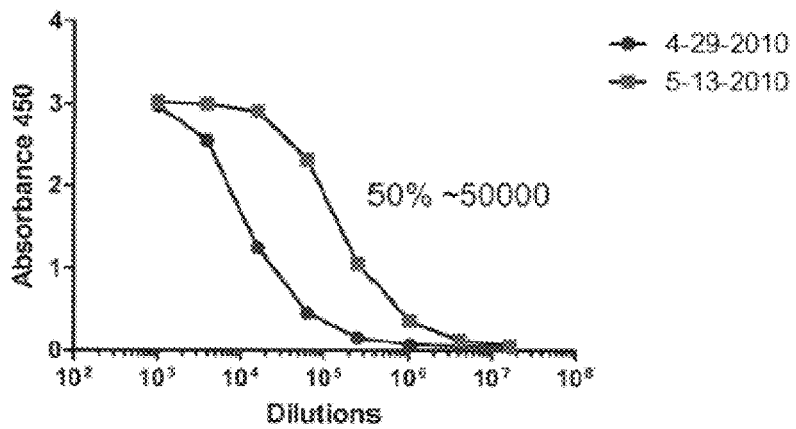

FIGURE 5

SEQ ID NO: 1

```
ATGGTCCCCAGGCTCTGCTCTTCGTGCCTTTGCTGGTCTTCCCACTCTGCTTGGGAAGTTCCCATCTACACC
ATCCCTGACAAGCTGGGCCCCTGGTCCCCTATCGACATCCACCACCTGTCTTGCCCTAACAACCTGGTGGTCGAG
GACGAAGGCTGCACTAACTTGTCCGGATTCTCTTACATGGAGCTCAAAGTGGGTTACATCTCCGCTATCAAGATG
AACGGCTTCACTTGCACCGGAGTGGTCACCGAGGCCGAAACTTACACCAACTTCGTGGGCTACGTCACTACACC
TTCAAGAGAAGCACTTCAGACCAACTCCCGACCGCTTGCAGGGCTGCCTACAACTGGAAGATGGCCGGAGACCCA
AGATACGAGGAATCCCTGCACAACCCTTACCCAGACTACCACTGGCTGGTACCGGAAGACTACCAAGCAGTCC
CTGGTCATCATCTCTCCATCTGTGGCTGACCTTGGACCCTACGACCGTAGCTTGCACTCAAGAGTCTTCCCAGGT
GGAAACTGCAGCGGAGTGGCCGTCTCCTCTACTTACTGCTCAACCAACCACGACTACACTATCTGGATGCCAGAG
AACCCCCGCCTGGGCATGAGCTGCGACATCTTCACCAACTCACTGGGAAGCGCGGCCTGCAAGGGTTCTGAGACT
TGCGGCTTCGGGGACGAAAGGGGTTTGTACAAGTCCCTGAAGGGCGCCTTGCAAGCTCAAGTTGTGCGGCCTGTC
GGACTCAGATTGATGGACGGCACCTGGGTCGCCATGCAGACTAGCAACGAGACCAAGTGGTGCCCCGGACAA
CTCGTCAACTTGCACGACTTCCGTTCAGACGAGATCGAACACCTGGTGGTCGAGGAACTGGTCAAGAAGCGCGAG
GAATGCCTGGACGCTCTCGAGAGCATCATGACTACCAAGAGCGTGTCATTCGTGCCTCGCACACTTAGGAAG
CTCGTCCCCGGTTTCGGCAAGGCCTACACTATCTTCAACAAGACCCTCATGGAGGCTGACGCCCACTACAAGTCC
GTCCGTACCTGGAACGAAATCATCCCCTCTAAGGGTTGCCTGGTGTCGGAGGTAGATGCCACCCTCACGTGAAC
GGAGTCTTCTTCAACGGTATCATCCTGGGTCCTGACGGCAACGTGCTCATCCCAGAGATGCAAAGCTCACTCTTG
CAGCAACACATGGAACTGCTCGTGTCCTCTGTCATCCCTCTCATGCACCCATTGGTTGACCCCAGTACCGTCTTC
AAGAACGGCGACGAGGCCGAAGACTTCGTGGAGGTGCACTTGCCAGACGTGCACGAACGCATCTCCGGAGTCGAC
CTGGGTCTCCCAACTGGGAAAGTACGTGTTGCTGTCTCCTGGTGCCTCACCGCTTTGATGCTGATCATCTTC
TTGATGACTTGCTGGAGGAGTCAACAGGTCTGAGCCTACTCAGCACAACCTGAGGGGAACTGGTAGAGAAGTC
TCCGTCACTCCACAATCTGGAAAGATCATCAGCTCATGGGAGAGCTACAAGTCAGGCGGAGAAACCGGTCTG
TAA
```

SEQ ID NO: 2

```
MVPQALLFVPLLVFPLCFGKFPIYTIPDKLGPWSPIDIHHLSCPNNLVVEDEGCTNLSGF
SYMELKVGYISAIKMNGFTCTGVVTEAETYTNFVGYVTTTFKRKHFRPTPDACRAAYNWK
MAGDPRYEESLHNPYPDYHWLRTVKTTKESLVIISPSVADLDPYDRSLHSRVFPGGNCSG
VAVSSTYCSTNHDYTIWMPENPRLGMSCDIFTNSRGKSAKGSETCGFVDERGLYKSLKG
ACKLKLCGVLGLRLMDGTWVAMQTSNETKWCPPGQLVNLHDFRSDEIEHLVVEELVKKRE
ECLDALESIMTTKSVSFRRLSHLRKLVPGFGKAYTIFNKTLMEADAHYKSVRTWNEIIPS
KGCLVGGRCHPHVNGVFFNGIILGPDGNVLIPEMQSSLLQQHMELLVSSVIPLMHPLAD
PSTVFKNGDEAEDFVEVHLPDVHERISGVDLGLPNWGKYVLLSAGALTALMLIIFLMTCW
RRVNRSEPTQHNLRCTGREVSVTPQSGKIISSWESYKGGETGL
```

RABIES GLYCOPROTEIN VIRUS-LIKE PARTICLES (VLPS)

CROSS REFERENCE TO RELATED APPLICATION

This application is a continuation of U.S. Ser. No. 13/883,745, filed Feb. 28, 2014, which is the U.S. national stage application of International Application No. PCT/US2011/059602, which was filed on Nov. 7, 2011 and claims priority to U.S. Provisional Application No. 61/410,767, filed Nov. 5, 2010, the disclosures of each are hereby incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_047_02US_SeqList.txt, date recorded: Jun. 29, 2017, file size 7 kilobytes).

TECHNICAL FIELD

The present invention is generally related to virus-like particles (VLPs) comprising rabies virus (RV) glycoproteins (G proteins) and methods for making and using them, including immunogenic compositions such as vaccines for the treatment and/or prevention of rabies virus infection.

BACKGROUND OF THE INVENTION

Rabies virus (RV) is a non-segmented negative-stranded RNA virus of the Rhabdoviridae family and induces a fatal neurological disease in humans and animals. More than 70,000 human fatalities are reported annually and millions of others require post-exposure treatment. Although significant advances have been made in rabies prevention and control, the disease remains a major threat to public health and continues to cause numerous human deaths around the world. Canines remain the most important reservoir in Asia, Africa and Latin America where most human rabies cases occur. In the developed countries, human rabies has declined significantly during the past 50 years, primarily as a result of routine vaccination of pet animals. However, rabies transmission via exposure to wild-life has emerged as a major cause of the disease. In the United States, more than 90% of animal rabies cases have been reported in wildlife, representing continual public health threats. Most human cases in the past decade have been associated with RV found in bats, particularly silver-haired bats.

Rhabdoviruses have two major structural components: a helical ribonucleoprotein core (RNP) and a surrounding envelope. The rabies genome encodes five proteins: nucleoprotein (N), phosphoprotein (P), matrix protein (M), glycoprotein (G) and polymerase (large protein) (L). The order of the genes in the wild-type rabies genome is 3'-N-P-M-G-L-5'. The N, L and P proteins are associated with the core RNP complex. The RNP complex consists of the RNA genome encapsidated by the N in combination with polymerase L and the P protein. This complex serves as a template for virus transcription and replication. The viral envelope component of RV is composed of a transmembrane glycoprotein (G) and a matrix (M) protein. The glycoprotein forms approximately 400 trimeric spikes which are tightly arranged on the surface of the virus. The M protein is associated both with the envelope and the RNP and may be the central protein of rhabdovirus assembly.

As noted above, rabies remains a major public health threat around the world. Controlling rabies and protecting humans from rabies requires several control strategies, such as routine immunization of pet animals and wildlife carriers, pre-exposure immunization of people at risk, and post-exposure treatment of people bitten by rabid animals. Although inactivated rabies virus (RV) vaccines prepared from cell culture are safe and well-tolerated, they have multiple disadvantages. They are difficult to manufacture, difficult to store, have low immunogenicity, and require multiple injections. Moreover, they are expensive and thus beyond the reach of most people who need the vaccines in the developing countries. In addition, these inactivated vaccines typically include adjuvants which may cause unwanted side effects. Thus, safer, cheaper, and more efficacious RV vaccines are needed.

The present application addresses this need through the development of a novel method for the production of virus-like particles (VLPs) comprising the rabies glycoprotein (G).

SUMMARY OF THE INVENTION

The present invention relates to rabies virus (RV) virus-like particles (VLPs) for use in vaccines for the treatment and prevention of rabies virus infection. The RV VLPs of the invention have the potential to induce potent immune responses in mammalian subjects against the rabies virus.

In a first aspect, the present invention provides RV VLPs comprising one or more RV glycoproteins (G proteins). The RV G proteins may be derived from any suitable RV strain, including, but not limited to, human, canine, bat, raccoon, skunk, and fox strains of RV. In one embodiment, the RV VLPs comprising one or more RV G proteins may be in the form of micelles. In some embodiments, the RV VLPs may comprise one or more additional RV proteins, selected from the nucleoprotein (N), phosphoprotein (P), matrix protein (M), and polymerase (large protein) (L). In a specific embodiment, the RV VLPs of the present invention may comprise the RV matrix protein (M). In one embodiment, the M protein is derived from a human strain of RV. In another embodiment, the M protein is derived from a canine strain of RV. In yet another embodiment, the M protein is derived from a bat strain of RV. In other embodiments, the matrix protein may be an M1 protein from an influenza virus strain. In one embodiment, the influenza virus strain is an avian influenza virus strain. In other embodiments, the M protein may be derived from a Newcastle Disease Virus (NDV) strain.

In one embodiment, the coding sequence of the RV G protein is further optimized to enhance its expression in a suitable host cell. In one embodiment, the host cell is an insect cell. In an exemplary embodiment, the insect cell is an Sf9 cell.

The RV VLPs of the present invention may be used for the prevention and/or treatment of RV infection. Thus, in another aspect, the invention provides a method for eliciting an immune response against RV. The method involves administering an immunologically effective amount of a composition containing a RV VLP to a subject, such as a human or animal subject.

In another aspect, the present invention provides pharmaceutically acceptable vaccine compositions comprising an RV VLP which comprises one or more RV glycoproteins (G proteins).

In one embodiment, the invention comprises an immunogenic formulation comprising at least one effective dose of an RV VLP which comprises one or more RV glycoproteins (G proteins). In another embodiment, the invention provides for a pharmaceutical pack or kit comprising one or more containers filled with one or more of the ingredients of the vaccine formulations of the invention.

In another embodiment, the invention provides a method of formulating a vaccine or antigenic composition that induces immunity to an infection or at least one disease symptom thereof to a mammal, comprising adding to the formulation an effective dose of an RV VLP which comprises one or more RV glycoproteins (G proteins). In a preferred embodiment, the infection is an RV infection.

The RV VLPs of the invention are useful for preparing compositions that stimulate an immune response that confers immunity or substantial immunity to infectious agents. Thus, in one embodiment, the invention provides a method of inducing immunity to infections or at least one disease symptom thereof in a subject, comprising administering at least one effective dose of an RV VLP which comprises one or more RV glycoproteins (G proteins).

In yet another aspect, the invention provides a method of inducing substantial immunity to RV infection or at least one disease symptom in a subject, comprising administering at least one effective dose of an RV VLP which comprises one or more RV glycoproteins (G proteins).

Compositions of the invention can induce substantial immunity in a vertebrate (e.g. a human or a canine) when administered to the vertebrate. Thus, in one embodiment, the invention provides a method of inducing substantial immunity to RV infection or at least one disease symptom in a subject, comprising administering at least one effective dose of an RV VLP which comprises one or more RV glycoproteins (G proteins). In another embodiment, the invention provides a method of vaccinating a mammal against RV comprising administering to the mammal a protection-inducing amount of an RV VLP which comprises one or more RV glycoproteins (G proteins). The prophylactic vaccine formulation is systemically administered, e.g., by subcutaneous or intramuscular injection using a needle and syringe, or a needle-less injection device. In an exemplary embodiment, the vaccine formulation is administered intramuscularly.

In another embodiment, the invention comprises a method of inducing a protective antibody response to an infection or at least one symptom thereof in a subject, comprising administering at least one effective dose of an RV VLP which comprises one or more RV glycoproteins (G proteins).

In another embodiment, the invention comprises a method of inducing a protective cellular response to RV infection or at least one disease symptom in a subject, comprising administering at least one effective dose of an RV VLP which comprises one or more RV glycoproteins (G proteins).

In yet another aspect, the invention provides an isolated nucleic acid encoding a rabies glycoprotein (G protein). In an exemplary embodiment, the isolated nucleic acid encoding a rabies glycoprotein (G protein) protein is SEQ ID NO: 1.

In yet another aspect, the invention provides an isolated cell comprising a nucleic acid encoding a rabies glycoprotein (G protein). In an exemplary embodiment, the isolated nucleic acid encoding a rabies glycoprotein (G protein) protein is SEQ ID NO: 1.

In yet another aspect, the invention provides a vector comprising a nucleic acid encoding a rabies glycoprotein (G protein). In an exemplary embodiment, the isolated nucleic acid encoding a rabies glycoprotein (G protein) protein is SEQ ID NO: 1. In one embodiment, the vector is a baculovirus vector.

In yet another aspect, the invention provides a method of making a RV VLP comprising one or more rabies glycoproteins (G proteins), comprising (a) transforming a host cell to express a nucleic acid encoding a rabies glycoprotein (G protein); and (b) culturing said host cell under conditions conducive to the production of said RV VLPs. In one embodiment, the nucleic acid encoding a rabies glycoprotein (G protein) is SEQ ID NO: 1. In another embodiment, the host cell is an insect cell. In a further embodiment, the host cell is an is an insect cell transfected with a baculovirus vector comprising a rabies glycoprotein (G protein).

BRIEF DESCRIPTION OF THE FIGURES

FIG. 2 depicts the results of western blotting for RV G proteins using anti-RV rabbit sera under both reducing (FIG. 2A) and non-reducing conditions (FIG. 2B).

FIG. 4 depicts the results of antibody-induction assays in rabbits administered increasing dilutions of RV G particles.

FIG. 5 shows the protein sequence for the pFastBac1 vector comprising the rabies virus G nucliec acid sequence (SEQ ID NO: 1) (top) and the RV G protein sequence (SEQ ID NO: 2) (bottom).

DETAILED DESCRIPTION

Definitions

Figure 1:
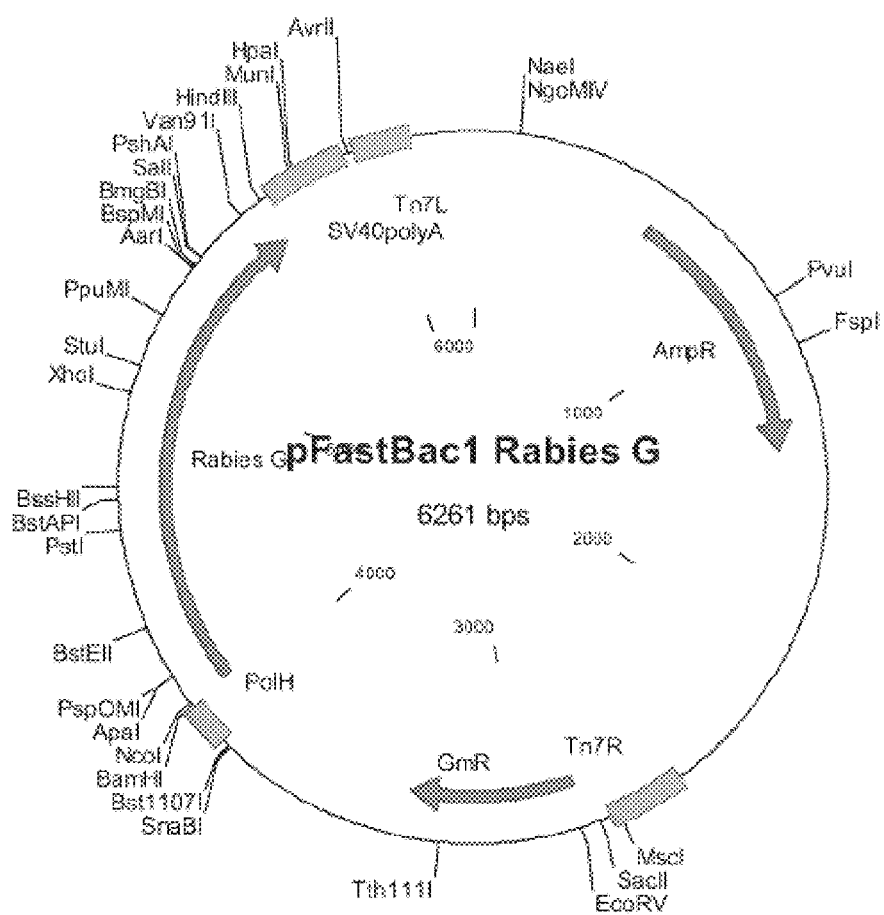
FIG. 1 depicts the plasmid map for the pFastBac1 vector comprising the rabies virus G nucleic acid sequence (SEQ ID NO: 1).

As used herein the term "adjuvant" refers to a compound that, when used in combination with a specific immunogen (e.g. an RV VLP which comprises one or more RV glycoproteins (G proteins)) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

As use herein, the term "antigenic formulation" or "antigenic composition" refers to a preparation which, when administered to a vertebrate, especially a bird or a mammal, will induce an immune response.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity) emerges, spreading beyond individual localities, possibly around the globe, and infecting many humans at once.

As used herein an "effective dose" generally refers to that amount of an RV VLP which comprises one or more RV glycoproteins (G proteins) sufficient to induce immunity, to prevent and/or ameliorate an infection or to reduce at least one symptom of an infection or disease, and/or to enhance the efficacy of another dose of an RV VLP which comprises one or more RV glycoproteins (G proteins). An effective dose may refer to the amount of an RV VLP which comprises one or more RV glycoproteins (G proteins) sufficient to delay or minimize the onset of an infection or disease. An effective dose may also refer to the amount of an RV VLP which comprises one or more RV glycoproteins (G proteins) that provides a therapeutic benefit in the treatment or management of an infection or disease. Further, an effective dose is the amount with respect to an RV VLP which comprises one or more RV glycoproteins (G proteins) alone, or in combination with other therapies, that provides a therapeutic benefit in the treatment or management of an infection or disease. An effective dose may also be the amount sufficient to enhance a subject's (e.g., a human's) own immune response against a subsequent exposure to an infectious agent or disease. Levels of immunity can be monitored, e.g., by measuring amounts of neutralizing secretory and/or serum antibodies, e.g., by plaque neutralization, complement fixation, enzyme-linked immunosorbent, or microneutralization assay, or by measuring cellular responses, such as, but not limited to cytotoxic T cells, antigen presenting cells, helper T cells, dendritic cells and/or other cellular responses. T cell responses can be monitored, e.g., by measuring, for example, the amount of $CD4^+$ and $CD8^+$ cells present using specific markers by fluorescent flow cytometry or T cell assays, such as but not limited to T-cell proliferation assay, T-cell cytotoxic assay, TETRAMER assay, and/or ELISPOT assay. In the case of a vaccine, an "effective dose" is one that prevents disease and/or reduces the severity of symptoms.

As used herein, the term "effective amount" refers to an amount of an RV VLP which comprises one or more RV glycoproteins (G proteins) necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to an RV VLP which comprises one or more RV glycoproteins (G proteins). The term is also synonymous with "sufficient amount." In another embodiment, the effective amount is the amount by weight of a RV G micelle that enduces seroprotection in a relevant animal model, animal or human patient in a desired number of days, e.g. 7, 10, 14 or more days.

As used herein, the term "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA. In the context of the present invention, the term also encompasses the yield of RV G gene mRNA and RV G proteins achieved following expression thereof.

As used herein, the term "G protein" or "G glycoprotein" or "G protein polypeptide" refers to a polypeptide or protein having all or part of an amino acid sequence of an RV G protein polypeptide.

As used herein, the terms "immunogens" or "antigens" refer to substances such as proteins, peptides, peptides, nucleic acids that are capable of eliciting an immune response. Both terms also encompass epitopes, and are used interchangeably.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons (IFN-γ), interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As use herein, the term "immunogenic formulation" refers to a preparation which, when administered to a vertebrate, e.g. a mammal, will induce an immune response.

As use herein, the term "infectious agent" refers to microorganisms that cause an infection in a vertebrate. Usually, the organisms are viruses, bacteria, parasites, protozoa and/or fungi.

As used herein, the term "multivalent" refers to compositions which have one or more antigenic proteins/peptides or immunogens against multiple types or strains of infectious agents or diseases, e.g. more than one RV G protein type, strain, sequence, etc.

As used herein, the term "pharmaceutically acceptable vaccine" refers to a formulation which contains an RV VLP which comprises one or more RV glycoproteins (G proteins), which is in a form that is capable of being administered to a vertebrate and which induces a protective immune response sufficient to induce immunity to prevent and/or ameliorate an infection or disease, and/or to reduce at least one symptom of an infection or disease, and/or to enhance the efficacy of another dose of an RV VLP which comprises one or more RV glycoproteins (G proteins). Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

As used herein, the phrase "protective immune response" or "protective response" refers to an immune response mediated by antibodies against an infectious agent or disease, which is exhibited by a vertebrate (e.g., a human), that prevents or ameliorates an infection or reduces at least one disease symptom thereof. An RV VLP of the present invention which comprises one or more RV glycoproteins (G proteins) can stimulate the production of antibodies that, for example, neutralize infectious agents, blocks infectious agents from entering cells, blocks replication of the infectious agents, and/or protect host cells from infection and destruction. The term can also refer to an immune response that is mediated by T-lymphocytes and/or other white blood cells against an infectious agent or disease, exhibited by a vertebrate (e.g., a human), that prevents or ameliorates infection or disease, or reduces at least one symptom thereof.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered. In particular, humans, domestic mammals, and farm animals are appropriate recipients of an RV vaccine or therapeutic.

As used herein, the term "virus-like particle" (VLP) refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

As used herein, the term "chimeric VLP" refers to VLPs that contain proteins, or portions thereof, from at least two different infectious agents (heterologous proteins). Usually, one of the proteins is derived from a virus that can drive the formation of VLPs from host cells. Examples, for illustrative purposes, are the avian influenza M protein and/or the RV G protein. The terms RV VLPs and chimeric VLPs can be used interchangeably where appropriate.

As used herein, the term "vaccine" refers to a preparation of dead or weakened pathogens, or of derived antigenic determinants that is used to induce formation of antibodies or immunity against the pathogen. A vaccine is given to provide immunity to the disease, for example, influenza, which is caused by influenza viruses. In addition, the term "vaccine" also refers to a suspension or solution of an immunogen (e.g. an RV VLP which comprises one or more RV glycoproteins (G proteins)) that is administered to a vertebrate to produce protective immunity, i.e., immunity that prevents or reduces the severity of disease associated with infection. The present invention provides for vaccine compositions that are immunogenic and may provide protection against a disease associated with infection.

Rabies Virus (RV) Virus-Like Particles (VLPs)

In one aspect, the invention relates RV virus-like particles (VLPs) comprising one or more RV glycoproteins (G proteins) that can be formulated into vaccines or antigenic formulations for protecting vertebrates (e.g. humans and domestic animals) against RV infection or at least one disease symptom thereof. In some embodiments, the VLP comprising one or more RV glycoproteins (G proteins) further comprises additional RV proteins, such as N, P, M, and L. In other embodiments, the VLP comprising one or more RV glycoproteins (G proteins) further comprises proteins from heterologous strains of virus, such as influenza virus proteins HA, NA, and M1. In one embodiment, the influenza virus protein M1 is derived from an avian influenza virus strain (see U.S. application Ser. No. 13/280,043, which is incorporated herein by reference in its entirety).

RV Vaccines

Since RV infection can be prevented by providing neutralizing antibodies to a vertebrate, a vaccine comprising an RV VLP which comprises one or more RV glycoproteins (G proteins) may induce, when administered to a vertebrate, neutralizing antibodies in vivo. The RV VLPs which comprise one or more RV glycoproteins (G proteins) are favorably used for the prevention and/or treatment of RV infection. Thus, another aspect of this disclosure concerns a method for eliciting an immune response against RV. The method involves administering an immunologically effective amount of a composition containing an RV VLP which comprises one or more RV glycoproteins (G proteins) to a subject (such as a human or animal subject). Administration of an immunologically effective amount of the composition elicits an immune response specific for epitopes present on the RV G protein. Such an immune response can include B cell responses (e.g., the production of neutralizing antibodies) and/or T cell responses (e.g., the production of cytokines). Preferably, the immune response elicited by the RV G protein includes elements that are specific for at least one conformational epitope present on the RV G protein. In one embodiment, the immune response is specific for an epitope present on an RV G protein found in the micelle conformation. The RV G proteins and compositions can be administered to a subject without enhancing viral disease following contact with RV. Preferably, the RV G proteins disclosed herein and suitably formulated immunogenic compositions elicit a Th1 biased immune response that reduces or prevents infection with a RV and/or reduces or prevents a pathological response following infection with a RV.

In one embodiment, the RV G proteins of the present invention are found in the form of micelles (e.g. rosettes). See example 2. In one embodiment, the micelles are purified following expression in a host cell. When administered to a subject, the micelles of the present invention preferably induce neutralizing antibodies. In some embodiments, the micelles may be administered with an adjuvant. In other embodiments, the micelles may be administered without an adjuvant.

In another embodiment, the invention encompasses RV virus-like particles (VLPs) comprising a RV G protein that can be formulated into vaccines or antigenic formulations for protecting vertebrates (e.g. humans) against RV infection or at least one disease symptom thereof. The present invention also relates to RV VLPs and vectors comprising wild-type and mutated RV genes or a combination thereof derived from different strains of RV virus, which when transfected into host cells, will produce virus like particles (VLPs) comprising RV proteins.

In some embodiments, RV virus-like particles may further comprise at least one viral matrix protein (e.g. an RV M protein). In one embodiment, the M protein is derived from a human strain of RV. In another embodiment, the M protein is derived from an alternative strain of RV, such as a canine, bat, raccoon, or skunk strain of RV. In other embodiments, the matrix protein may be an M1 protein from a strain of influenza virus. In one embodiment, the strain of influenza virus is an avian influenza strain. In an exemplary embodiment, the avian influenza strain is the H5N1 strain A/Indonesia/5/05. In other embodiments, the matrix protein may be from Newcastle Disease Virus (NDV).

In further embodiments, VLPs of the invention may comprise one or more heterologous immunogens, such as influenza hemagglutinin (HA) and/or neuraminidase (NA).

In some embodiments, the invention also comprises combinations of different RV G, N, P, M, and L proteins from the same and/or different strains in one or more VLPs. In addition, the VLPs can include one or more additional molecules for the enhancement of an immune response.

In another embodiment of the invention, the RV VLPs can carry agents such as nucleic acids, siRNA, microRNA, chemotherapeutic agents, imaging agents, and/or other agents that need to be delivered to a patient.

VLPs of the invention are useful for preparing vaccines and immunogenic compositions. One important feature of VLPs is the ability to express surface proteins of interest so that the immune system of a vertebrate induces an immune response against the protein of interest. However, not all proteins can be expressed on the surface of VLPs. There may be many reasons why certain proteins are not expressed, or be poorly expressed, on the surface of VLPs. One reason is that the protein is not directed to the membrane of a host cell or that the protein does not have a transmembrane domain. As an example, sequences near the carboxyl terminus of influenza hemagglutinin may be important for incorporation of HA into the lipid bilayer of the mature influenza enveloped nucleocapsids and for the assembly of HA trimer interaction with the influenza matrix protein M1 (Ali, et al., (2000) J. Virol. 74, 8709-19).

Thus, one embodiment of the invention comprises chimeric VLPs comprising a G protein from RV and at least one immunogen which is not normally efficiently expressed on the cell surface or is not a normal RV protein. In one embodiment, the RV G protein may be fused with an immunogen of interest. In another embodiment, the RV G protein associates with the immunogen via the transmembrane domain and cytoplasmic tail of a heterologous viral surface membrane protein, e.g., MMTV envelope protein.

Other chimeric VLPs of the invention comprise VLPs comprising a RV G protein and at least one protein from a heterologous infectious agent. Examples of heterologous infectious agent include but are not limited to a virus, a bacterium, a protozoan, a fungi and/or a parasite. In one embodiment, the immunogen from another infectious agent is a heterologous viral protein. In another embodiment, the protein from a heterologous infectious agent is an envelope-associated protein. In another embodiment, the protein from another heterologous infectious agent is expressed on the surface of VLPs. In another embodiment, the protein from an infectious agent comprises an epitope that will generate a protective immune response in a vertebrate. In one embodiment, the protein from another infectious agent is co-expressed with a RV G protein. In another embodiment, the protein from another infectious agent is fused to a RV G protein. In another embodiment, only a portion of a protein from another infectious agent is fused to a RV G protein. In another embodiment, only a portion of a protein from another infectious agent is fused to a portion of a RV G protein. In another embodiment, the portion of the protein from another infectious agent fused to a RV G protein is expressed on the surface of VLPs.

The invention also encompasses variants of the proteins expressed on or in the VLPs of the invention. The variants may contain alterations in the amino acid sequences of the constituent proteins. The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to mutations in the proteins. These mutations may lead to antigenic variability within individual groups of infectious agents, for example influenza. Thus, a person infected with, for example, an influenza strain develops antibody against that virus, as newer virus strains appear, the antibodies against the older strains no longer recognize the newer virus and re-infection can occur. The invention encompasses all antigenic and genetic variability of proteins from infectious agents for making VLPs.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating of RV G molecules, etc. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises protein variants which show substantial biological activity, e.g., able to elicit an effective antibody response when expressed on or in VLPs of the invention. Such variants include deletions, insertions, inversions, repeats, and substitutions selected according to general rules known in the art so as have little effect on activity.

Methods of cloning the proteins are known in the art. For example, the gene encoding a specific RV protein can be isolated by RT-PCR from polyadenylated mRNA extracted from cells which had been infected with rabies virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the nucleotides encode for a RV G protein (as discussed above). In another embodiment, the vector further comprises nucleotides that encode the RV M protein. In another embodiment, the vector further comprises nucleotides that encode the M and/or N RV proteins. In another embodiment, the vector further comprises nucleotides that encode the M, L and/or N RV proteins. In an exemplary embodiment, the expression vector is a baculovirus vector.

In some embodiments of the invention, proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells. See U.S. Patent Publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the RV viral proteins can be cloned. A person with skill in the art understands that additional methods are available and are possible.

The invention also provides for constructs and/or vectors that comprise RV nucleotides that encode for RV structural genes, including G, M, N, L, P, or portions thereof, and/or any chimeric molecule described above. The vector may be, for example, a phage, plasmid, viral, or retroviral vector. The constructs and/or vectors that comprise RV structural genes, including G, M, N, L, P, or portions thereof, and/or any chimeric molecule described above, should be operatively linked to an appropriate promoter, such as the AcMNPV polyhedrin promoter (or other baculovirus), phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan. In one embodiment, the vector that comprises nucleotides encoding for RV genes, including RV G genes, as well as genes for M, N, L, P, or portions thereof, and/or any chimeric molecule described above, is pFastBac.

The recombinant constructs mentioned above could be used to transfect, infect, or transform and can express RV proteins, including a RV G protein and at least one immunogen. In one embodiment, the recombinant construct comprises a RV G, M, N, L, P, or portions thereof, and/or any molecule described above, into eukaryotic cells and/or prokaryotic cells. Thus, the invention provides for host cells which comprise a vector (or vectors) that contain nucleic acids which code for RV structural genes, including a RV G; and at least one immunogen such as but not limited to RV N, L, and P, or portions thereof, and/or any molecule described above, and permit the expression of genes, including RV G, N, L, or P or portions thereof, and/or any molecule described above in the host cell under conditions which allow the formation of VLPs.

Among eukaryotic host cells are yeast, insect, avian, plant, *C. elegans* (or nematode) and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. *Xenopus laevis oocytes*, or other cells of amphibian origin, may also be used. Examples of prokaryotic host cells include bacterial cells, for example, *E. coli, B. subtilis, Salmonella typhi* and mycobacteria.

Vectors, e.g., vectors comprising polynucleotides of a RV G protein; and at least one immunogen including but not limited to RV N, L, P, or portions thereof, and/or any chimeric molecule described above, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the vector is a recombinant baculovirus. In another embodiment, the recombinant baculovirus is transfected into a eukaryotic cell. In a preferred embodiment, the cell is an insect cell. In another embodiment, the insect cell is a Sf9 cell.

This invention also provides for constructs and methods that will increase the efficiency of VLP production. For example, the addition of leader sequences to the RV G, M, N, L, P, or portions thereof, and/or any chimeric or heterologous molecules described above, can improve the efficiency of protein transporting within the cell. For example, a heterologous signal sequence can be fused to the RV G, M, N, L, P, or portions thereof, and/or any chimeric or heterologous molecule described above. In one embodiment, the signal sequence can be derived from the gene of an insect cell and fused to the RV G, M, N, L, P, or portions thereof, and/or any chimeric or heterologous molecules described above. In another embodiment, the signal peptide is the chitinase signal sequence, which works efficiently in baculovirus expression systems.

Another method to increase efficiency of VLP production is to codon optimize the nucleotides that encode RV including a RV G protein, M, N, L, P, or portions thereof, and/or any chimeric or heterologous molecules described above for a specific cell type. In one embodiment, nucleic acids are codon optimized for expression in insect cells. In an exemplary embodiment, the insect cells are Sf9 insect cells.

The invention also provides for methods of producing VLPs, the methods comprising expressing RV genes including a RV G protein under conditions that allow VLP formation. Depending on the expression system and host cell selected, the VLPs are produced by growing host cells transformed by an expression vector under conditions whereby the recombinant proteins are expressed and VLPs are formed. In one embodiment, the invention comprises a method of producing a VLP, comprising transfecting vectors encoding at least RV G protein into a suitable host cell and expressing the RV G protein under conditions that allow VLP formation. In another embodiment, the eukaryotic cell is selected from the group consisting of, yeast, insect, amphibian, avian or mammalian cells. The selection of the appropriate growth conditions is within the skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 1000 L bags.

The VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. Usually VLPs are produced from recombinant cell lines engineered to create VLPs when the cells are grown in cell culture (see above). A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, the cells are infected with recombinant baculovirus at the most efficient multiplicity of infection (e.g. from about 1 to about 3 plaque forming units per cell). Once infection has occurred, the RV G protein, and/or any chimeric or heterologous molecule described above, are expressed from the virus genome, self assemble into VLPs and are secreted from the cells approximately 24 to 72 hours post infection. Usually, infection is most efficient when the cells are in mid-log phase of growth ($4\text{-}8\times10^6$ cells/ml) and are at least about 90% viable.

VLPs can be harvested approximately 48 to 96 hours post infection, when the levels of VLPs in the cell culture medium are near the maximum but before extensive cell lysis. The Sf9 cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 µm filter cartridge or a similar device.

Next, VLPs in the clarified culture medium can be concentrated by ultra-filtration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at $6,500\times g$ for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant RV VLPs can be accomplished in insect cells, for example Sf9 insect cells as previously described. In one embodiment, the cells are Sf9 infected with recombinant baculovirus engineered to produce RV VLPs.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and an RV VLP which comprises one or more RV glycoproteins (G proteins). As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

The invention encompasses a pharmaceutically acceptable vaccine composition comprising an RV VLP which comprises one or more RV glycoproteins (G proteins). In one embodiment, the pharmaceutically acceptable vaccine composition comprises VLPs comprising at least one RV G protein and at least one additional immunogen. In another embodiment, the pharmaceutically acceptable vaccine composition comprises VLPs comprising at least one RV G protein and at least one RV M protein. In another embodiment, the pharmaceutically acceptable vaccine composition comprises VLPs comprising at least one RV G protein and at least one influenza M protein. In another embodiment, the pharmaceutically acceptable vaccine composition comprises VLPs comprising at least one RV G protein and at least one avian influenza M1 protein.

The invention also encompasses a kit for immunizing a vertebrate, such as a human subject, comprising VLPs that comprise at least one RV G protein.

In one embodiment, the invention comprises an immunogenic formulation comprising at least one effective dose of an RV VLP which comprises one or more RV glycoproteins (G proteins).

The immunogenic formulation of the invention comprises an RV VLP which comprises one or more RV glycoproteins (G proteins), and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention also provides for a pharmaceutical pack or kit comprising one or more containers filled with one or more of the ingredients of the vaccine formulations of the invention. In one embodiment, the kit comprises two containers, one containing an RV VLP which comprises one or more RV glycoproteins (G proteins), and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the formulation be packaged in a hermetically sealed container such as an ampoule or sachette indicating the quantity of composition. In one embodiment, the composition is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the composition is supplied in liquid form in a hermetically sealed container indicating the quantity and concentration of the composition. Preferably, the liquid form of the composition is supplied in a hermetically sealed container at least about 50 µg/ml, more preferably at least about 100 µg/ml, at least about 200 µg/ml, at least 500 µg/ml, or at least 1 mg/ml.

As an example, RV VLPs comprising one or more RV G proteins are administered in an effective amount or quantity (as defined above) sufficient to stimulate an immune response, each a response against one or more strains of RV. Administration of the RV VLP which comprises one or more RV glycoproteins (G proteins) elicits immunity against RV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. In an exemplary embodiment, the vaccine formulation is administered intramuscularly.

Thus, the invention also comprises a method of formulating a vaccine or antigenic composition that induces immunity to an infection or at least one disease symptom thereof to a mammal, comprising adding to the formulation an effective dose of an RV VLP which comprises one or more RV glycoproteins (G proteins). In one embodiment, the infection is an RV infection.

While stimulation of immunity with a single dose is possible, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections, e.g. RV infection. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Methods of administering a composition comprising an RV VLP which comprises one or more RV glycoproteins (G proteins) (e.g. vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents.

Vaccines and/or immunogenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, the compositions of the invention can be administered as part of a combination therapy. For example, compositions of the invention can be formulated with other immunogenic compositions, antivirals and/or antibiotics.

The dosage of the pharmaceutical composition can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. The dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. an RV VLP which comprises one or more RV glycoproteins (G proteins), to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and a carrier for the antigen. In another embodiment, the vesicles are primarily made of nonphospholipid vesicles. In other embodiment, the vesicles are Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant for influenza antigens (see, U.S. Pat. Nos. 5,629,021, 6,387,373, and 4,911,928, herein incorporated by reference in their entireties for all purposes).

The compositions of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the compositions of the invention, or can be administered separately. Either the protein or an expression vector encoding the protein can be administered to produce an immunostimulatory effect. Thus in one embodiment, the invention comprises antigentic and vaccine formulations comprising an adjuvant and/or an immune stimulator.

Methods of Stimulating an Immune Response

The RV VLPs which comprise one or more RV glycoproteins (G proteins) are useful for preparing compositions that stimulate an immune response that confers immunity or substantial immunity to infectious agents. The invention encompasses a method of inducing immunity to infections or at least one disease symptom thereof in a subject, comprising administering at least one effective dose of an RV VLP which comprises one or more RV glycoproteins (G proteins).

In one aspect, the invention comprises a method to induce immunity to RV infection or at least one disease symptom thereof in a subject, comprising administering at least one effective dose of an RV VLP which comprises one or more RV glycoproteins (G proteins). In one embodiment, the subject is a vertebrate. In another embodiment, the vertebrate is a mammal. In yet another embodiment, the mammal is a human. In yet another embodiment, the mammal is a domestic animal. In another embodiment, the method comprises inducing immunity to RV infection or at least one disease symptom by administering the formulation in one dose. In another embodiment, the method comprises inducing immunity to RV infection or at least one disease symptom by administering the formulation in multiple doses.

Compositions of the invention can induce substantial immunity in a vertebrate (e.g. a human) when administered to the vertebrate. The substantial immunity results from an immune response against compositions of the invention that protects or ameliorates infection or at least reduces a symptom of infection in the vertebrate. In some instances, if the vertebrate is infected, the infection will be asymptomatic. The response may not be a fully protective response. In this case, if the vertebrate is infected with an infectious agent, the vertebrate will experience reduced symptoms or a shorter duration of symptoms compared to a non-immunized vertebrate.

In another embodiment, the invention comprises a method of inducing a protective antibody response to an infection or at least one symptom thereof in a subject, comprising administering at least one effective dose of an RV VLP which comprises one or more RV glycoproteins (G proteins).

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

In one embodiment, the invention comprises a method of inducing a protective cellular response to RV infection or at least one disease symptom in a subject, comprising administering at least one effective dose of RV VLP which comprises one or more RV glycoproteins (G proteins).

As mentioned above, the immunogenic compositions of the invention prevent or reduce at least one symptom of RV infection in a subject. Symptoms of RV are well known in the art. They include fever, headache, and general weakness or discomfort. As the disease progresses, more specific symptoms appear and may include insomnia, anxiety, confusion, slight or partial paralysis, excitation, hallucinations, agitation, hypersalivation (increase in saliva), difficulty swallowing, and hydrophobia (fear of water). Thus, the method of the invention comprises the prevention or reduction of at least one symptom associated with RV infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a RV infection or additional symptoms, a reduced severity of a RV symptoms or a suitable assays (e.g. antibody titer and/or T-cell activation assay). The objective assessment comprises both animal and human assessments.

This invention is further illustrated by the following examples that should not be construed as limiting. The contents of all references, patents and published patent applications cited throughout this application, as well as the Figures and the Sequence Listing, are incorporated herein by reference for all purposes.

EXAMPLES

Example 1

Purification of Rabies G Particles for Animal Study

The purpose of this Example is to demonstrate how RV G virus-like particles were purified following expression from baculovirus vectors in Sf9 insect cells.

To construct RV VLPs, the nucleic acid sequence encoding the RV G protein (SEQ ID NO: 2) was expressed from the baculovirus vector (pFastBac1 Rabies G) shown in FIG. 1.

Sf9 insect cells were infected at $2.5 \times 10^6$ cell/ml with a MOI of 0.2. Cells were harvested at 69 hrs post-infection by centrifuge at 4000 g for 15 mins. Cells were washed with 1×PBS, spun again, and frozen at −70° C.

A 23 gram cell pellet was used obtained from an approximately 2 L cell culture. The cell pellet was resuspended with 200 ml 25 mM TrisCL pH 8.0, 50 mM NaCl, 0.5% NP9, 4 ug/mL leupeptin. It was stirred at room temperature for 1 hr, spun at 7000 g for 60 mins at 4° C., and 200 ml supernatent was saved for chromatography.

Upon completion of Rabies G839 extraction from cell pellet, the soluble proteins were loaded onto a Fractogel EMD TMAE Hicap (M) chromatography column. The specifications of the column were as follows: Column manufacturer: GE Healthcare; Column type: XK50f20; Resin manufacturer: EMD Chemicals; Resin type: Fractogel EMD TMAE Hicap (M); Packed column dimensions: approximately 10 cm height×5.0 cm diameter; Packed column volume: 200 ml; Packing flow rate: 30 ml/min; Packing buffer: 25 mM Tris pH 8.0/300 mM NaCl.

The specifications of the anion exchange process were as follows: Running flow rate: 20 ml/min; Column equilibration buffer: 25 mM Tris pH 8.0, 50 mM NaCl, 0.02% NP9; Eluent A: 25 mM Tris pH 8.0, 50 mM NaCl, 0.02% NP9; Eluent B1: 25 mM Tris pH 8.0, 180 mM NaCl, 0.02% NP9; Eluent B2: 25 mM Tris pH 8.0, 500 mM NaCl, 0.02% NP9; Eluent B3: 25 mM Tris pH 8.0, 1500 mM NaCl, 0.02% NP9; Column load: 200 ml of Rabies G VLP extraction supernatant; Column wash after load: 2 CV eluent A; Column elution: 2 CV eluent BI, 2 CV eluent B2, 2 CV eluent B3.

The major fraction collection and volumes were as follows: Flow-through fraction: 250 mL; B1 180 mM NaCl elution: 175 ml (product); B2 500 mM NaCl elution: 100 ml; B3 1500 mM NaCl elution: 100 ml.

The 180 mM NaCl elution fraction of the TMAE column was loaded onto a lentil lectin column. The specifications of the column were as follows: Column manufacturer: GE Healthcare; Column type: XKI6/20; Resin manufacturer: GE Healthcare; Resin type: Lentil Lectin Sepharose 4B; Resin catalog #: 17-0444-01; Packed column dimensions: 2.5 cm height×1.6 cm diameter; Packed column volume: approximately 5 ml; Packing flow rate: 2.5 ml/min; Packing buffer: 25 mM $NaHPO_4$ pH6.8, 50 mM NaCl, 0.02% NP9; Running flow rate: 2 mL/min; Column equilibration buffer: 25 mM $NaHPO_4$ pH6.8, 50 mM NaCl, 0.02% NP9; Eluent A: 25 mM $NaHPO_4$ pH6.8, 50 mM NaCl, 0.02% NP9, Eluent B: 25 mM $NaHPO_4$ pH6.8, 50 mM NaCl, 0.02% NP9, 500 mM Methyl-alpha-Dmannopyronoside (Fisher Scientific); Column load: 175 ml of Rabies G839 TMAE 180 mM NaCl elution; Column wash after load: 5 CV with eluent A; Column elution: 10 CV with eluent B;

The major fraction collection and volumes were as follows: Flow-through fraction: 180 ml; Elution fraction: 30 ml (product).

The lentil lectin elution was loaded onto a Fractogel EMD SO3—Hicap (M) chromatography column. The specifications of the column were as follows: Column manufacturer: GE Healthcare; Column type: XK16/20; Resin manufacturer: EMD Chemicals; Resin type: Fractogel EMD SO3—Hicap (M); Packed column dimensions: 5 cm height×1.6 cm diameter; Packed column volume: 10 ml; Packing flow rate: 7.5 ml/min; Packing buffer: 25 mM $NaHPO_4$ pH 6.8, 50 mM NaCl, 0.02% NP9

The specifications of the cation exchange process were as follows: Running flow rate: 5 mL/min; Column equilibration buffer: 25 mM $NaHPO_4$ pH 6.8, 50 mM NaCl, 0.02% NP9; Eluent A: 25 mM $NaHPO_4$ pH 6.8, 50 mM NaCl, 0.02% NP9; Eluent B: 25 mM $NaHPO_4$ pH 6.8, 300 mM NaCl, 0.02% NP9; Column load: 30 mL of Rabies G839 lectin lectin elution; Column wash after load: 3 CV with eluent A; Column elution: 4 CV step elution eluent B; Major fraction collection and volumes: Elution fraction: 9 ml (final product); Filter 9 ml SO3—column 300 mM NaCl elution product with 0.2 μm filter: Filter manufacture (0.2 μm): Corning; Filter type: 28 mm syringe filter with a 0.2 micron SFCA membrane.

Western blotting using anti-RV G rabbit sera were performed (FIG. 2). The purity of RV G particles using the above-conditions was 86%. The total protein amount was 0.39 mg/ml, and the concentration of RV G particles was 0.33 mg/ml, with a total of 2.97 mg RV G particles from a 2 L cell culture, with a a yield of approximately 1.5 mg/L cell culture. Importantly, RV G particles were stable at 4° C. for at least one month (data not shown).

Example 2

Electron Microscopy for Analysis of RV G Protein Conformation

Figure 3:
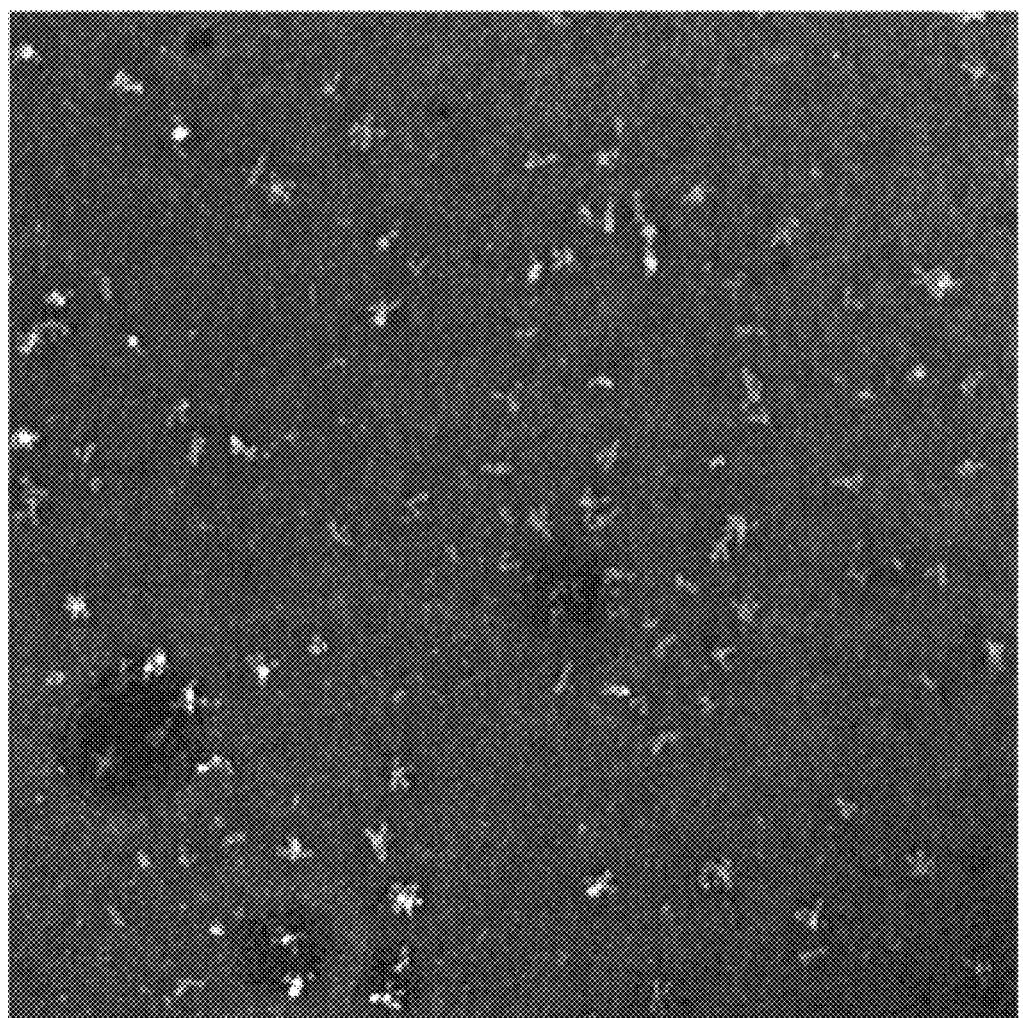
FIG. 3 depicts images of purified recombinant RV G protein particles in the forms of micelles taken using negative stain electron microscopy at a magnification of 150,000×.

Purified RV G protein was analyzed by negative stain electron microscopy (see FIG. 3). The average molecular weight of the RV G particles with 0.02% NP9 was $1.04 \times 10^{-6}$. The protein trimers exhibited a molecular weight of 175.5 kDa and the average number of trimers in a particle was 5.9. The RV G proteins aggregated in the form of micelles (rosettes). The fact that the G spikes exhibit micelle morphology under electron microscopy suggests that the G protein particles have the correct 3-dimensional structure of a native protein.

Example 3

RV G Particles Induce High Antibody Levels in Rabbits

To test the ability of RV G particles to induce an immune response, rabbits were administered RV G particles at varying concentrations. The results of these experiments are illustrated in FIG. 4. RV G particles were able to induce high levels of antibodies in rabbits.

Example 4

RV Neutralization Assay and RV Challenge Studies in Mice

To test the efficiency of a vaccine comprising RV VLPs comprising one or more G proteins in protecting against RV infection, neutralization assays are conducted in mice. Briefly, groups of mice are injected intramuscularly with RV VLPs or RV VLPs+an adjuvant, such as aluminum. In addition, mice are injected with Rabipur®, a commercially available inactivated rabies virus vaccine, which is used as a comparative vaccine agent. RV VLPs comprising one or more G proteins (i.e. RV G micelles) are generally expected to induce higher titers of neutralizing antibodies when compared with Rabipur®.

Example 5

Comparison of Anti-Rabies Titer in Balb/c Mice Injected with Either RV G Particles or Commercial Rabies Vaccine Rabipur®

The immunogenecity of the VLPs of the present invention was compared to the commercial rabies vaccine Rabipur® in a Balb/c mouse model. RV G VLP particles were constructed and purified as described in Example 1. The VLPs aggregated in the form of micelles (FIG. 3).

The study included four groups (n=5 for each group):

Group I: positive control (commercial rabies vaccine Rabipur®)

Group II: RV G VLP (5 μg)

Group III: RV G VLP (2 μg)

Group IV: RVG VLP (1 μg)

Mice were administered the respective immunogen at 0.1 mL at days 0, 3 and 7. Serum samples were taken from the mice at days 0, 4, 7, 10, 14, 21, 28, 35. Serum was tested for neutralizing anti-rabies antibodies by ELISA.

A summary of the study design is given in table 1 below.

TABLE 1

Study design

| Parameter | Anti-rabies titer in serum by ELISA (neutralizing) | | | |
|---|---|---|---|---|
| Analytes | Serum | | | |
| Identification | Group I<br>Positive control | Group II<br>Test 1 | Group III<br>Test 2 | Group IV<br>Test 3 |
| Number of mice | 5 | 5 | 5 | 5 |
| Immunogen | Commercial rabies vaccine Rabipur ® | RV G VLP (5 µg) | RV G VLP (2 µg) | RV G VLP (1 µg) |
| Schedule for immunization | 0.1 mL, I/D, Day 0, 3, 7 | | | |
| Bleeds (days) | 0, 4, 7, 10, 14, 21, 28, 35 | | | |
| Analyte | Serum for neutralizing anti-rabies virus titer | | | |

Figure 6:
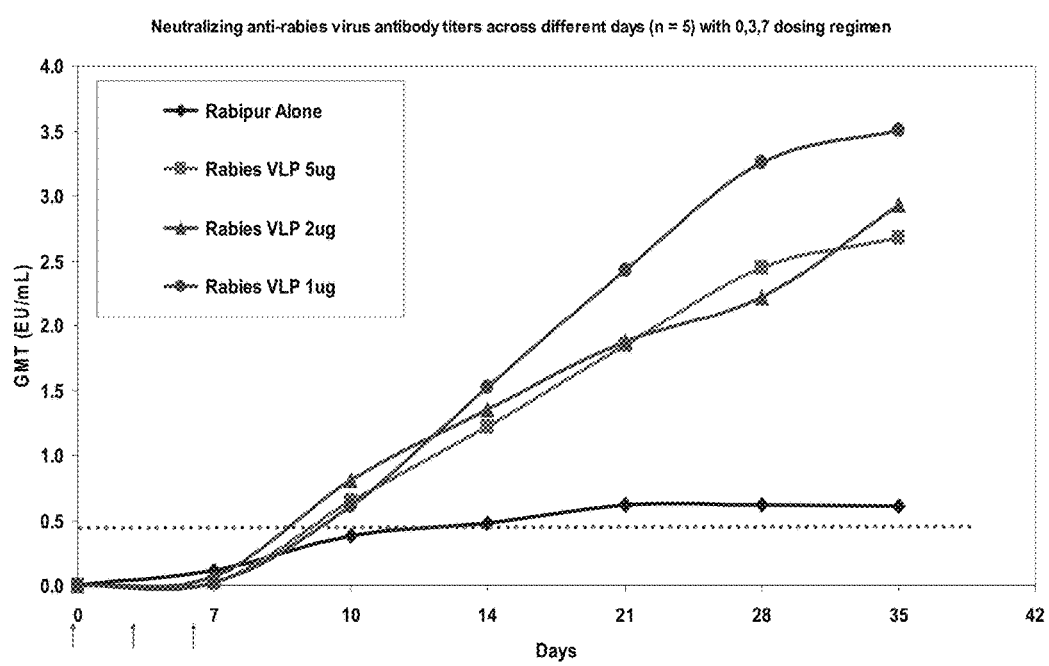
FIG. 6 is a graph showing the anti-rabies virus antibody titers at different days, plotted as the geometric mean for each immunization regimen (n=5 for each immunization group).

As discussed above, anti-rabies neutralizing antibodies were measured in mouse sera at the time points provided above. The titers were plotted as the geometric mean for each measurement (FIG. 6). As FIG. 6 shows, the VLP micelles of the present invention, at each dosage, provide more rapid and higher antibody titers than the commercially available vaccine, Rabipur®. Specifically, the RV G VLP provided a sero-protection titer (0.5 EU/mL) days earlier than the Rabipur® vaccine (FIG. 6, Table 2).

Table 2 also shows the percent sero-protection (i.e., a neutralizing antibody titer of ≥0.5 EU/mL) for each immunization group. The table indicates that sero-protection occurs more rapidly in animals treated with the RV G VLP of the present invention (at all three dosages), compared to animals administered Rabipur® vaccine.

TABLE 2

Percent sero-protection for each immunization group.

| | % Sero-protection on day (n = 5) | | | | | | |
|---|---|---|---|---|---|---|---|
| Identification | 0 | 7 | 10 | 14 | 21 | 28 | 35 |
| Rabipur ® alone (Group I) | 0 | 0 | 40 | 60 | 60 | 60 | 60 |
| RV G VLP (5 µg) (Group II) | 0 | 0 | 60 | 100 | 100 | 100 | 100 |
| RV G VLP (2 µg) (Group III) | 0 | 40 | 80 | 100 | 100 | 100 | 100 |
| RV G VLP (1 µg) | 0 | 0 | 60 | 100 | 100 | 100 | 100 |

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Although the application has been broken into sections to direct the reader's attention to specific embodiments, such sections should be not be construed as a division amongst embodiments. The teachings of each section and the embodiments described therein are applicable to other sections.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of making a micelle particle comprising rabies virus (RV) glycoprotein (G protein), wherein the G proteins form a trimer, comprising:
   (a) transforming an Sf9 cell to express a nucleic acid encoding a RV G protein; and
   (b) culturing said Sf9 cell under conditions conducive to the production of said RV G protein trimers; and
   (c) purifying a micelle particle comprising the RV G protein trimers in the presence of NP-9 detergent.

2. The method according to claim 1, wherein said Sf9 cell is transfected with a baculovirus vector comprising a nucleic acid comprising SEQ ID NO:1.

3. The method according to claim 1, wherein said Sf9 cell is transfected with a baculovirus vector comprising a nucleic acid that encodes a RV G protein comprising SEQ ID NO:2.

4. The method according to claim 1, wherein step (c) comprises lentil lectin affinity chromatography.

5. The method according to 1, wherein step (c) comprises:
   (a) anion exchange chromatography;
   (b) cation exchange chromatography; and
   (c) lentil lectin affinity chromatography.

6. The method according to claim 5, wherein the anion exchange chromatography utilizes an elution buffer comprising 25 mM Tris pH 8.0, 180 mM NaCl, and 0.02% NP-9.

7. The method according to claim 5, wherein the cation exchange chromatography utilizes an elution buffer comprising 25 mM NaHPO$_4$ pH 6.8, 300 mM NaCl, and 0.02% NP-9.

8. The method according to claim 5, wherein the lentil lectin affinity chromatography utilizes an elution buffer comprising 25 mM NaHPO$_4$ pH 6.8, 50 mM NaCl, 500 mM Methyl-α-D-mannopyranoside and 0.02% NP-9.

9. The method according to claim 1, wherein the G protein trimer forms spikes on the surface of the micelle particle.

10. The method according to claim 1, wherein the RV G protein is derived from an RV strain selected from human, canine, bat, raccoon, skunk, and fox.

11. The method according to claim 1, wherein the micelle particle is stored in a buffer comprising 25 mM NaHPO$_4$ pH 6.8, 300 mM NaCl, and 0.02% NP-9.

12. A pharmaceutical composition comprising the micelle particle comprising rabies virus (RV) glycoprotein (G protein), wherein the G proteins form a trimer; 25 mM NaHPO$_4$ pH 6.8, 300 mM NaCl, and 0.02% NP-9.

13. The composition of claim 12 further comprising an adjuvant.

14. The composition of claim 13, wherein the adjuvant is alum.

* * * * *

SEQUENCE LISTING

```
<160> NUMBER OF SEQ ID NOS: 2

<210> SEQ ID NO 1
<211> LENGTH: 1575
<212> TYPE: DNA
<213> ORGANISM: Rabies virus

<400> SEQUENCE: 1
atggtgcccc aggctctgct cttcgtgcct ttgctggtct tcccactctg cttcggcaag      60
ttccccatct acaccatccc tgacaagctg ggcccctggt cccctatcga catccaccac     120
ttgtcttgcc ctaacaacct ggtggtcgag gacgaaggct gcactaactt gtccggattc     180
tcttacatgg agctgaaagt gggttacatc tccgctatca agatgaacgg cttcacttgc     240
accggagtgg tcaccgaggc cgaaacttac accaacttcg tgggctacgt caccactacc     300
ttcaagagga agcacttcag accaactccc gacgcttgca gggctgccta caactggaag     360
```

-continued

```
atggccggag acccaagata cgaggaatcc ctgcacaacc cttacccaga ctaccactgg    420
ctccgtaccg tgaagactac caaggagtcc ctggtcatca tctccccatc tgtcgctgac    480
ctcgacccct acgaccgtag cttgcactca agagtcttcc caggtggaaa ctgcagcgga    540
gtggccgtct cctctactta ctgctcaacc aaccacgact acactatctg gatgccagag    600
aacccccgcc tgggcatgag ctgcgacatc ttcaccaact cacgtggaaa gcgcgcctcc    660
aagggttctg agacttgcgg cttcgtggac gaaaggggtt tgtacaagtc cctgaagggc    720
gcttgcaagc tcaagttgtg cggcgtgctg ggactcagat tgatggacgg cacctgggtc    780
gccatgcaga ctagcaacga gaccaagtgg tgcccccctg gacaactcgt gaacttgcac    840
gacttccgtt cagacgagat cgaacacctg gtggtcgagg aactcgtcaa gaagcgcgag    900
gaatgcctgg acgctctcga gagcatcatg actaccaaga gcgtgtcatt ccgtcgcttg    960
tcacacctga ggaagctcgt ccccggtttc ggcaaggcct acactatctt caacaagacc   1020
ctcatggagg ctgacgccca ctacaagtcc gtgcgtacct ggaacgaaat catcccctct   1080
aagggttgcc tgcgtgtcgg aggtagatgc caccctcacg tgaacggagt cttcttcaac   1140
ggtatcatcc tgggtcctga cggcaacgtg ctcatcccag agatgcaaag ctcactcttg   1200
cagcaacaca tggaactgct cgtgtcctct gtcatccctc tcatgcaccc attggctgac   1260
cccagcaccg tcttcaagaa cggcgacgag gccgaagact tcgtggaggt ccacctgcca   1320
gacgtgcacg aacgcatctc cggagtcgac ctgggtctcc ccaactgggg aaagtacgtg   1380
ttgctgtctg ctggtgccct caccgctttg atgctgatca tcttcttgat gacttgctgg   1440
aggagagtca acaggtctga gcctactcag cacaacctga ggggaaccgg tagagaagtg   1500
tccgtcactc cacaatctgg aaagatcatc agctcatggg agagctacaa gtcaggcgga   1560
gaaaccggtc tgtaa                                                    1575
```

<210> SEQ ID NO 2
<211> LENGTH: 524
<212> TYPE: PRT
<213> ORGANISM: Rabies virus

<400> SEQUENCE: 2

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
```

```
            145                 150                 155                 160
Leu Asp Pro Tyr Asp Arg Ser Leu His Ser Arg Val Phe Pro Gly Gly
                    165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Val Ser Ser Val Ile Pro Leu Met His
                405                 410                 415

Pro Leu Ala Asp Pro Ser Thr Val Phe Lys Asn Gly Asp Glu Ala Glu
            420                 425                 430

Asp Phe Val Glu Val His Leu Pro Asp Val His Glu Arg Ile Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Trp
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser Tyr Lys Ser Gly Gly Glu Thr Gly Leu
        515                 520
```